(12) United States Patent
Bogojevic et al.

(10) Patent No.: US 7,863,566 B2
(45) Date of Patent: Jan. 4, 2011

(54) MEDICAL X-RAY DETECTION DEVICE INCLUDING AN ACTIVE OPTICAL SIGNAL EMITTER

(75) Inventors: Aleksander Bogojevic, Munich (DE); Manfred Weiser, Munich (DE)

(73) Assignee: BrainLAB AG, Feldkirchen (DE)

( * ) Notice: Subject to any disclaimer, the term of this patent is extended or adjusted under 35 U.S.C. 154(b) by 153 days.

(21) Appl. No.: 11/677,230

(22) Filed: Feb. 21, 2007

(65) Prior Publication Data

US 2007/0195933 A1 Aug. 23, 2007

Related U.S. Application Data

(60) Provisional application No. 60/777,071, filed on Feb. 27, 2006.

(30) Foreign Application Priority Data

Feb. 21, 2006 (EP) .................. 06003498

(51) Int. Cl.
*G01T 1/00* (2006.01)
*H05G 1/00* (2006.01)
(52) U.S. Cl. .............. 250/336.1; 250/370.09; 378/95; 378/117; 378/205
(58) Field of Classification Search ............. 250/336.1, 250/370.09; 378/95, 98, 117, 205
See application file for complete search history.

(56) References Cited

U.S. PATENT DOCUMENTS

| | | | | |
|---|---|---|---|---|
| 3,952,199 A * | 4/1976 | Franke | ............. | 378/116 |
| 4,012,638 A * | 3/1977 | Altschuler et al. | ......... | 378/170 |
| 4,918,714 A * | 4/1990 | Adamski et al. | ............ | 378/121 |
| 4,935,950 A * | 6/1990 | Ranallo et al. | .............. | 378/207 |
| 5,081,663 A * | 1/1992 | Gerlach et al. | .............. | 378/207 |
| 6,236,712 B1 * | 5/2001 | Tomasetti et al. | ........... | 378/114 |
| 6,470,207 B1 * | 10/2002 | Simon et al. | ................ | 600/426 |
| 2005/0242289 A1 * | 11/2005 | Grichnik et al. | ........ | 250/370.07 |

FOREIGN PATENT DOCUMENTS

EP  1 260 179 B1  3/2003
JP  04 065694  3/1992

\* cited by examiner

*Primary Examiner*—David P Porta
*Assistant Examiner*—Jessica L Eley
(74) *Attorney, Agent, or Firm*—Renner, Otto, Boisselle & Sklar, LLP

(57) ABSTRACT

A medical x-ray detection device includes an x-ray detector operable to detect the presence of x-ray radiation in a medical environment, and a signal emitter operatively coupled to said x-ray detector. The signal emitter includes at least one active light-emitting signal device, wherein the signal emitter is operative to emit a signal corresponding to the presence of x-ray radiation.

21 Claims, 1 Drawing Sheet

MEDICAL X-RAY DETECTION DEVICE INCLUDING AN ACTIVE OPTICAL SIGNAL EMITTER

RELATED APPLICATION DATA

This application claims priority of U.S. Provisional Application No. 60/777,071 filed on Feb. 27, 2006, which is incorporated herein by reference in its entirety.

FIELD OF THE INVENTION

The invention relates to a medical x-ray detection method, device and system, wherein an x-ray detector detects the presence of x-ray radiation in a medical environment, and a signal emitter emits a signal with respect to the detected x-ray radiation.

BACKGROUND OF THE INVENTION

In many cases x-ray detection devices are used when registering x-ray images within the context of medical navigation. Such devices enable the determination of when (and therefore the relative position of the patient) the image was produced so as to allow the image to be correctly assigned within the context of navigation. It is of course in principle also possible to transmit the detection signal to a receiver via cable, e.g., to a further processing unit, such as a navigation system. Such cables, however, typically are laid or otherwise provided separate in the x-ray device or registration device and, therefore, necessitate additional interfaces on the signal receiving components, which increases overall system complexity.

Another conventional approach for applications with analog x-ray image generating systems is to update the image information and to re-register when there are changes in the image contents. Such a system is known, for example, from EP 1 260 179 B1; however, many older or specific operating x-ray apparatus are still in use whose signal-to-noise ratio makes such a procedure difficult to implement or does not permit such a procedure. In cases in which the image is directly manipulated on the x-ray apparatus (e.g., scaled, rotated, flipped or contrast-enhanced), this could also lead to a "new" image being detected even though this is not the case. As a result, navigation problems may arise.

SUMMARY OF THE INVENTION

A signal emitter includes an active light-emitting signal means, and an x-ray detector, which is operatively coupled to the signal emitter. The x-ray detector can detect the start and/or end of x-ray radiation and provide the data to the signal emitter, wherein the signal emitter emits corresponding signals. In other words, the signal emitter emits an optical signal (e.g., active light emissions), which can be directly detected without time lag, such that the presence of the x-ray radiation can be reliably detected temporally.

The signal means can include an LED and, in particular, can be an infrared emitter or an infrared LED. Using light in the infrared spectrum is advantageous in that disturbance by light flashes in the visible light spectrum have no effect on signal detection. It is noted, however, that the signal emitter also can function perfectly well with signal means that emit in the visible light spectrum. For example, it is conceivable to unambiguously identify the signal by the fact that it includes a particular signal sequence. When the "emission of light" is used within the context of the present disclosure, this includes visible light and/or non-visible light within the electromagnetic spectrum.

Power for the signal means can be provided in different ways. For example, an internal or dedicated power supply, such as, for example, a battery or rechargeable battery, may provide power to the signal means. It is also conceivable to generate the power for the signal means from the x-ray detector itself (from the x-ray radiation energy) and to relay the power directly to the signal means. In such an embodiment, a corresponding converter may be used to convert the x-ray radiation energy to DC power, for example.

In accordance with another aspect of the invention, a medical x-ray detection system can include an x-ray detection device such as described herein. The x-ray detection system also can include a fluoroscopic image registration unit, wherein the x-ray detector and the signal emitter are arranged on the fluoroscopic image registration unit. It is then possible to arrange the x-ray detector in the radiation transmission path of the fluoroscopic image registration unit. The x-ray detector, for example, can be arranged at a point at which it can reliably detect the presence of x-ray radiation. The signal emitter can be advantageously arranged on the outside of the fluoroscopic image registration unit, thereby enabling signal emissions to be easily detected by other externally mounted devices.

It is also possible to arrange several signal emitters on the fluoroscopic image registration unit. Further, several x-ray detectors can be arranged on the fluoroscopic image registration unit. This establishes a redundancy and provides for fail-safe operation. The fluoroscopic image registration unit, for example, can include three signal emitters and three x-ray detectors. These emitters and detectors can be assigned to each other in any possible way. Further, it is possible to have a single x-ray detector control several signal emitters, or to have one signal emitter controlled by several x-ray detectors.

Further, the one or more x-ray detection devices can be retrofitted or upgraded, wherein there exists the option of additionally providing a signal emitter or signal emitters and/or an x-ray detector or x-ray detectors on the fluoroscopic image registration unit such that they are attachable and detachable.

Further, a medical x-ray detection system can be provided that includes an x-ray detection device as described herein, as well as an optical medical tracking system, such as an infrared tracking system. The signal emitter can be arranged within the detection range of the tracking system. This is advantageous as the optical signal emitter can be easily and directly incorporated into the tracking system environment. Since such optical tracking systems are available or used in many navigation environments, the detection signal can be easily detected, processed and integrated into the sequence. Such a system (comprising a tracking system) can of course also comprise the features described herein for the medical x-ray detection system.

A method for x-ray detection includes detecting, via a detector unit, x-rays generated during treatment or treatment preparation. The information pertaining to the start and end of the radiation time can be relayed by an active component that can be embedded within an array of passive markers. The integration of passive and active light transmission is mutually supplemented here; both signals can be wirelessly transmitted and detected. While passive markers on a registration kit are perfectly sufficient for localizing such a kit, the active signal transmission for x-ray detection optimally supplements this information transmission. It is thus possible to incorporate trigger signals for the start or end of radiation, for example into a known navigation environment based on reflection marker technology. Integrating one or more x-ray detectors into the fluoroscopic image registration kit and supplementing the marker array of the kit with the signal emitter thus allows improved detection of newly acquired images, which incurs a high degree of reliability. Due to the control via this part of fluoroscopic image acquisition, all x-ray tracking or navigation systems can benefit from greatly reduced tracking errors. This applies to C-arm x-ray systems using analog image transmission (video), since the approach does not exhibit the drawbacks of purely software-based image comparison methods.

The apparatus, system and method described herein is particularly valuable in the environment of an infrared tracking system or a navigation system, since it optimally and precisely utilizes available systems that include passive marker arrays and infrared cameras. An additional active infrared component (signal emitter) would be automatically detected by the camera system, wherein the wavelength of the infrared light is within the detection range of the camera system, and its position would thus be available for further evaluation. Such an integration can be simply implemented by a few changes in the software responsible for detecting other treatment devices or treatment-assisting devices comprising positional markers, and the application itself could implement the corresponding algorithms. No changes need be made to the existing hardware.

Specifically for C-arm fluoroscopy apparatus having an analog transmission mode, automatic signal detection may be quickly and easily implemented. When the x-ray radiation is detected, the information from the image comparison, for example, can be supplemented with the trigger signal of the signal emitter. The exact time for storing the tracking information then can be ascertained from the coincidence criterion, in accordance with which both processes must take place at the same time, and within a very small time interval. A way of obtaining correct tracking information, which is more reliable in this way, also increases the safety and security of the patients.

BRIEF DESCRIPTION OF THE DRAWINGS

The forgoing and other features of the invention are hereinafter discussed with reference to the drawing.

DETAILED DESCRIPTION

Figure 1:
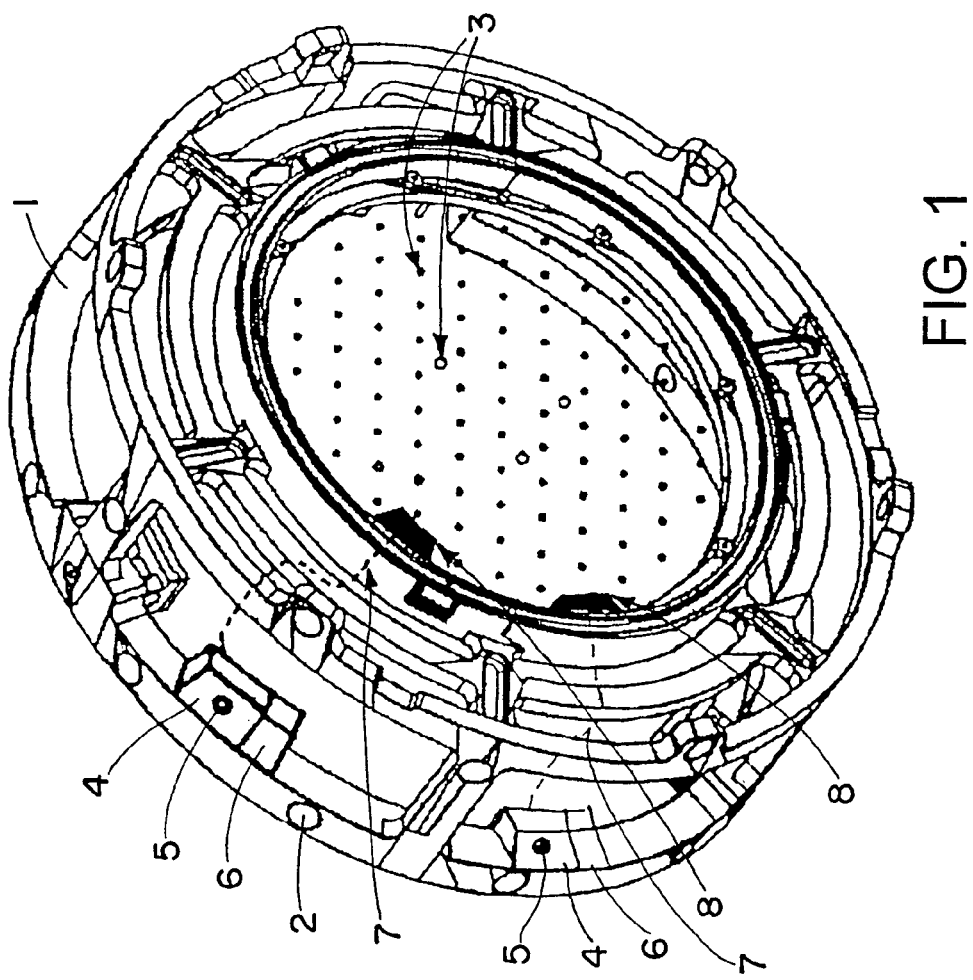
FIG. 1 shows an exemplary fluoroscopic registration kit including an x-ray detection device in accordance with the present invention.

The registration kit 1 shown in FIG. 1 can be a circular attachment for a image intensifier of a C-arm x-ray apparatus (fluoroscope). The kit 1 can include an insert in the radiation transmission path comprising tungsten spheres 3 for the internal registration of the projective properties and several passive reflection markers 2. The markers 2 can be provided in a specific arrangement and enable tracking of the kit 1 within a tracking and navigation environment.

Figure 2:
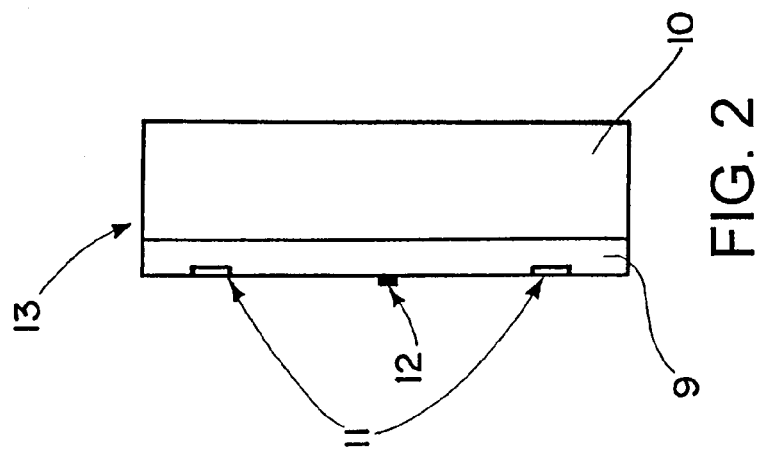
FIG. 2 is a schematic diagram of an exemplary tracking and navigation system that can be used with the present invention.

A tracking or navigation system 13 is schematically shown in FIG. 2. The system 13 can include a tracking system 9 and a navigation system 10 that processes and/or outputs tracking information (e.g., spatially localizing a treatment apparatus and a treatment-assisting apparatus, in particular spatially localizing and determining a location of the registration kit 1).

The tracking system 9 can include two cameras 11 and an infrared emitter 12. Infrared light from the emitter 12, for example, can be reflected by the refection markers 2 on the kit 1 and received by the cameras 11. The tracking system 9 then can calculate the spatial position of the kit 1 from these reception signals and relay the position to the navigation system 10 for processing.

A small x-ray detector 8 can be fixed to the inner circumference of the registration kit 1 (e.g., within the radiation transmission path). For example, the detector 8 can be fixed to a point in an outer region of the image intensifier plane that is close to the registration kit 1. Care should be taken that the detector does not disturb the fixation of the kit. This position allows x-rays to be detected, since it is applied in the shape of a cone, but does not substantially disturb the image contents.

On the opposite side of the registration kit 1, the active optical component (e.g., the signal emitter 4 comprising the active light-emitting signal means 5 which in the present example is an infrared LED) can be fixed on the outside of a lower protruding edge. In the advantageous embodiment shown here, the LED 5 is in a specific position, known in the navigation system 10, in relation to the reference system of the array of reflection markers 2. Additionally, an independent power supply is provided, e.g., a battery 6 (or rechargeable battery), and the detector 8 is connected via the line 7 to the unit including the signal emitter 4 and the battery 6. The battery can supply the necessary power for the signal emitter 4, and also for the detector 8.

When a new fluoroscopic image is acquired, radiation from an x-ray source is emitted in a conical shape onto an image intensifier. Since the detector 8 is fixed at a position that is not disturbed by the fixation of the kit 1, it can detect such radiation and trigger a signal that is emitted by the signal emitter 4, e.g., the LED 5. When the radiation falls below a particular threshold value, the trigger signal is stopped. By judiciously selecting the threshold value, a reliable measurement of the start and end time of the emitted radiation can be made, thereby avoiding false events originating from background radiation.

The optical trigger signal can be emitted by the LED 5 in the infrared wavelength range and therefore is visible to the tracking cameras 11 (which can be used for navigation). Since the position of the LED 5 in relation to the array of passive markers 2 can be known to the navigation system 10, the simultaneous observation of the marker array and the LED ensures that no arbitrary reflection is misinterpreted as a trigger signal.

In the navigation system 10, the tracking data of the cameras 11 or the tracking system 9 can be continuously updated and analyzed. If the marker geometry of the registration kit 1 is observed, an additional test for the presence of the signal from the LED 5 can be simply performed, for example, by testing whether the signal corresponds to an additional marker in a specific arrangement in relation to the reference frame of the registration kit 1.

In determining whether a new image has been acquired, two methods are presented. First, the time at which the signal is first detected can be recorded as the start time of radiation, and the time at which the signal is no longer observed is recorded as the end time. No other control need be performed, and the acquisition of a new image can be signalled to the system.

A second option is to correlate a trigger signal with another signal from the image comparison that is being performed in the background. A new image can be recognized if and only if both the trigger signal and the positive result of the image comparison are in temporal coincidence (with only a very small additional tolerance).

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A medical x-ray detection device, comprising:
   an x-ray detector operable to temporally detect the presence of x-ray radiation in a medical environment and output data indicative of said presence of x-ray radiation; and
   a signal emitter operatively coupled to said x-ray detector, the signal emitter including at least one active light-emitting signal device, wherein the signal emitter is operative to emit, based on the output data, a signal temporally corresponding to the presence of x-ray radiation as detected by the x-ray detector, wherein the light-emitting signal device emits light in the non-visible spectrum.

2. The medical x-ray detection device according to claim 1, wherein the light-emitting signal device comprises an LED.

3. The medical x-ray detection device according to claim 1, wherein the light-emitting signal device is connected to a power supply.

4. The medical x-ray detection device according to claim 3, wherein the power supply comprises a battery.

5. The medical x-ray detection device according to claim 1, wherein the x-ray detector is operative to detect a start and/or end of x-ray radiation, and the signal emitter is operative to emit at least one signal corresponding to the start and/or end of x-ray radiation.

6. A medical x-ray detection system, comprising:
   an x-ray detection device according to claim 1; and
   a fluoroscopic image registration unit, wherein the x-ray detector and the signal emitter are arranged on the fluoroscopic image registration unit.

7. The medical x-ray detection system according to claim 6, wherein the x-ray detector is arranged in a radiation transmission path of the fluoroscopic image registration unit.

8. The medical x-ray detection system according to claim 6, wherein the signal emitter is arranged on an outside portion of the fluoroscopic image registration unit.

9. The medical x-ray detection system according to claim 6, wherein a plurality of signal emitters are arranged on the fluoroscopic image registration unit.

10. The medical x-ray detection system according to claim 6, wherein a plurality of x-ray detectors are arranged on the fluoroscopic image registration unit.

11. The medical x-ray detection system according to claim 6, further comprising at least one additional signal emitter and/or at least one additional x-ray detector provided on the fluoroscopic image registration unit such that the additional signal emitter and/or detector are attachable and detachable to/from the fluoroscopic image registration unit.

12. The medical x-ray tracking system according to claim 6, further comprising at least one reflective marker arranged on the fluoroscopic image registration unit.

13. A medical x-ray detection system, comprising:
    an x-ray detection device according to claim 1; and
    an optical medical tracking system, wherein the signal emitter is arranged within a detection range of the medical tracking system.

14. The medical x-ray detection system of claim 13, wherein the medical tracking system comprises an infrared tracking system.

15. The medical x-ray detecting system according to claim 13, further comprising a medical navigation system, wherein the signal emitter is arranged in a specific position known by the medical navigation system.

16. The medical x-ray detecting system according to claim 15, wherein the medical navigation system is operative to detect a start and/or end of x-ray radiation based on a signal emitted by the signal emitter that corresponds to the start and/or end of x-ray radiation.

17. The medical x-ray detection device according to claim 1, wherein the signal emitter is operative to emit the signal in a particular sequence.

18. A medical x-ray detection device, comprising:
    an x-ray detector operable to temporally detect the presence of x-ray radiation in a medical environment and output data indicative of said presence of x-ray radiation; and
    a signal emitter operatively coupled to said x-ray detector, the signal emitter including at least one active light-emitting signal device, wherein the signal emitter is operative to emit, based on the output data, a signal temporally corresponding to the presence of x-ray radiation as detected by the x-ray detector, wherein the light-emitting signal device comprises an infrared emitter.

19. The medical x-ray detection device according to claim 18, wherein the infrared emitter comprises an infrared LED.

20. A method for providing an indication of the presence of x-rays in a medical environment, comprising:
    using an x-ray detector to temporally detect the presence of x-ray radiation in the medical environment; and
    using at least one active light-emitting signal device to provide a signal temporally corresponding to the presence of radiation as detected by the x-ray detector, wherein the signal is based on data indicative of the presence of x-ray radiation as provided by the x-ray detector, wherein the light-emitting signal device emits light in the non-visible spectrum.

21. A registration kit, comprising:
    an annular housing having an opening for placement in a radiation transmission path;
    an x-ray detector arranged on said housing and operable to temporally detect the presence of x-ray radiation in said opening and output data indicative of the presence of x-ray radiation; and
    a signal emitter operatively coupled to said x-ray detector, the signal emitter including at least one active light-emitting signal device, wherein the signal emitter is operative to emit, based on the output data, a signal temporally corresponding to the presence of x-ray radiation as detected by the x-ray detector.

* * * * *